(12) United States Patent
Werner et al.

(10) Patent No.: US 9,804,043 B2
(45) Date of Patent: Oct. 31, 2017

(54) MEASUREMENT OF VERY LOW TORQUE VALUES

(71) Applicants: Douglas Werner, Campbell, CA (US);
Adrian Correa, Campbell, CA (US);
James Earle, Campbell, CA (US)

(72) Inventors: Douglas Werner, Campbell, CA (US);
Adrian Correa, Campbell, CA (US);
James Earle, Campbell, CA (US)

(73) Assignee: BRUKER NANO INC., Santa Barbara, CA (US)

( * ) Notice: Subject to any disclaimer, the term of this patent is extended or adjusted under 35 U.S.C. 154(b) by 0 days.

(21) Appl. No.: 15/179,994

(22) Filed: Jun. 11, 2016

(65) Prior Publication Data

US 2016/0363494 A1    Dec. 15, 2016

Related U.S. Application Data

(60) Provisional application No. 62/175,220, filed on Jun. 13, 2015.

(51) Int. Cl.
| | |
|---|---|
| *G01L 3/00* | (2006.01) |
| *G01L 3/02* | (2006.01) |
| *G01N 19/02* | (2006.01) |
| *G01L 1/20* | (2006.01) |
| *G01B 7/13* | (2006.01) |

(52) U.S. Cl.
CPC .............. *G01L 3/02* (2013.01); *G01B 7/13* (2013.01); *G01L 1/205* (2013.01); *G01N 19/02* (2013.01)

(58) Field of Classification Search
CPC .. G01B 7/13; G01L 1/205; G01L 3/02; G01N 19/02

USPC .................................................. 73/862.08
See application file for complete search history.

(56) References Cited

U.S. PATENT DOCUMENTS

| | | | | |
|---|---|---|---|---|
| 5,335,556 A | * | 8/1994 | Mogilnicki | ............... G01L 5/24 29/721 |
| 8,387,450 B2 | * | 3/2013 | Ichige | ............... G01M 17/0072 73/116.06 |
| 2005/0216224 A1 | * | 9/2005 | Obunai | ............... G01M 17/022 702/145 |
| 2013/0125828 A1 | * | 5/2013 | Van Der Poel | ........ A01K 13/00 119/609 |
| 2014/0196619 A1 | * | 7/2014 | Kang | ..................... B41F 13/12 101/36 |
| 2015/0065309 A1 | * | 3/2015 | Bauer | .................... A63B 69/16 482/61 |

* cited by examiner

*Primary Examiner* — Max Noori

(57) ABSTRACT

A tangential force sensor is used instead of a coaxial strain gauge to measure the torque required to produce the rotation of a part. The force sensor is coupled tangentially to the rotating part through a non-slip contact produced by a force applied radially on the part. A progressively increasing tangential force produced by translating the force sensor in a direction normal to the axis of rotation of the part is then applied to initiate and maintain its rotation. The radial force applied to the part is judiciously selected and measured such that the part is engaged with enough friction to ensure a non-slip condition. By measuring the tangential force applied to the part, the torque characteristics of the rotatable part are determined. By sensing and controlling the radial force applied to the part, damage to the part or the mechanism supporting it is avoided.

20 Claims, 5 Drawing Sheets

ALIGN THE FORCE SENSOR OF A TORQUE-TESTING MECHANISM SUCH THAT IT MEASURES A FORCE TANGENT TO THE CYLINDRICAL SURFACE OF A ROTATABLE OBJECT TO BE MEASURED

↓

COUPLE A FLAT SURFACE OF THE FORCE SENSOR ASSEMBLY TANGENTIALLY TO THE OBJECT BY APPLYING A RADIAL FORCE THAT PRODUCES FRICTIONAL ENGAGEMENT WITH THE CYLINDRICAL SURFACE OF THE OBJECT

↓

TRANSLATE THE SENSOR ASSEMBLY RELATIVE TO THE OBJECT IN A DIRECTION NORMAL TO THE AXIS OF ROTATION OF THE OBJECT WHILE MAINTAINING FRICTIONAL CONTACT WITH THE OBJECT, SO AS TO INITIATE AND MAINTAIN THE ROTATION OF THE OBJECT

↓

MEASURE AND RECORD THE TANGENTIAL FORCE SO PRODUCED AND CANCULATE CORRESPONDING TORQUE VALUES

FIG. 5

MEASUREMENT OF VERY LOW TORQUE VALUES

RELATED APPLICATIONS

This application is based on and claims the priority of Provisional Application Ser. No. 62/175,220, filed Jun. 13, 2015, hereby incorporated by reference.

BACKGROUND OF THE INVENTION

Field of the Invention

The invention relates in general to the field of torque measurements and, in particular, to a novel approach to the measurement of a torque applied to the cylindrical component of a rotatable object.

Description of the Prior Art

Torque is the measure of the force that causes an object to rotate about an axis. When a tangential force is applied at a point of an object using a lever arm equal to the distance from the axis of rotation, torque is defined as the product of the force times the length of lever arm. In the case of a cylindrical object or mechanical part, such as a shaft rotating in a bearing, the tangential force is applied in some manner on the surface of the part and measured by some means.

Monitoring torque is sometimes critical to the performance of axles, drive trains, gear drives, electric and hydraulic motors, and gas and steam turbines, for example. Therefore, torque measurements are used routinely for quality control in the manufacture of rotating parts in order to ensure that design specifications are met. Such measurements are typically carried out using a strain gauge coupled to the object and to a driving motor. As illustrated schematically in FIG. 1, a test part 10, such as an axle supported by a bearing 12, is coupled by friction or other means axially to a strain gauge 14 through a shaft 16 attached to the gauge. The strain gauge is in turn coupled to a motor 18 through a connecting driving shaft 20. All parts need to be perfectly collinear with respect to the axis of rotation A of the part. As the motor 18 exerts a rotating force on the axle 10 through the shafts and the strain gauge 14, very small deformations within the gauge are detected and measured from which the torque applied to the axle is calculated. Typically, an increasing torque is applied to a stationary part and increased until rotation begins and reaches a constant speed with minimal torque application. A graph of applied torque versus circumferential distance is thus developed for the part so tested.

When very low torque values are measured, such as when a small part rotates within an air bearing driven device, the traditional approach to torque measurements is inadequate for quality-control purposes. For reliable results, the target torque values need to be orders of magnitude greater than any extraneous force affecting the measurement. However, ever present parasitic losses, such as produced by eddy currents in the system, and friction losses in the bearings supporting the mechanism acting on the part may be greater than the actual torque required to rotate the part. In addition, any misalignment along the axis of rotation between the various components of the measurement system (driving motor, shafts, strain gauge, and part) will produce forces or bending of components that will be detected by the strain gauge and mask the actual target torque value.

Another problem with conventional torque measurements of very low values lies in the sensitivity and size of the strain gauges required for such measurements. As the components of the measuring system are reduced in size to accommodate the measurement of very-low-torque parts, the signal-to-noise ratio may decrease beyond acceptable values as a result of the attendant added flexibility of the shaft holding the strain gauge. Under such conditions, the measurement yielded by the system would be uncertain and unreliable for repeatable quality-control purposes.

In view of these problems, prior-art measurement systems are not adequate for measuring parts that require the application of a very low torque to initiate and maintain their rotation. This invention is directed at providing a new approach that overcomes these problems with a mechanism suitable for inline quality-control purposes in manufacturing environments.

SUMMARY OF THE INVENTION

The invention lies in the idea of using a force sensor, preferably a two-dimensional force sensor, rather than a strain gauge, to measure the torque required to produce and maintain the rotation of a part. The 2-D force sensor is coupled tangentially to a cylindrical portion of the rotating part to be measured through a non-slip contact produced by a force that is applied radially on the part. A progressively increasing tangential force is then applied in some manner to initiate and maintain the rotation of the part. By measuring the tangential force so applied to the part, the torque required to produce and maintain the rotation of the part can be calculated simply by multiplying it by the radius of the cylindrical portion of the part.

The tangential force is produced by translating the sensor with respect to the part along a flat surface in tangential frictional contact with the part. The radial force applied to the part is judiciously selected and measured such that the flat surface and the part are coupled with enough friction to ensure a non-slip condition. By virtue of having a readily available measure of the radial force, the rotating part can be tested without applying excessive force that might damage the part or the mechanism supporting it. Appropriate materials are selected for contacting the part.

Various other advantages will become clear from the description of the invention in the specification that follows and from the novel features particularly pointed out in the appended claims. Therefore, this invention includes the features hereinafter illustrated in the drawings, fully described in the detailed description of the preferred embodiments and particularly pointed out in the claims, but such drawings and description disclose only some of the various ways in which the invention may be practiced.

BRIEF DESCRIPTION OF THE DRAWINGS

FIG. 5 is a flow chart of the steps involved in the procedure for measuring very low torques according to the invention.

DESCRIPTION OF THE PREFERRED EMBODIMENT

Strain gauges are devices that can be used to measure forces based on the strain applied to the gauge. The most common type consists of a metallic foil pattern that is deformed by the application of a force to the gauge. As a result of this deformation, the electrical resistance of the foil is changed, thereby providing a measure of the applied force. As mentioned, the heart of this invention is the idea of replacing coaxially-coupled strain gauges with tangentially-coupled force sensors to measure torque. The resulting approach eliminates parasitic losses and requires minimal collinear alignment, thereby greatly enhancing the sensitivity and precision of the measurement.

Figure 1:
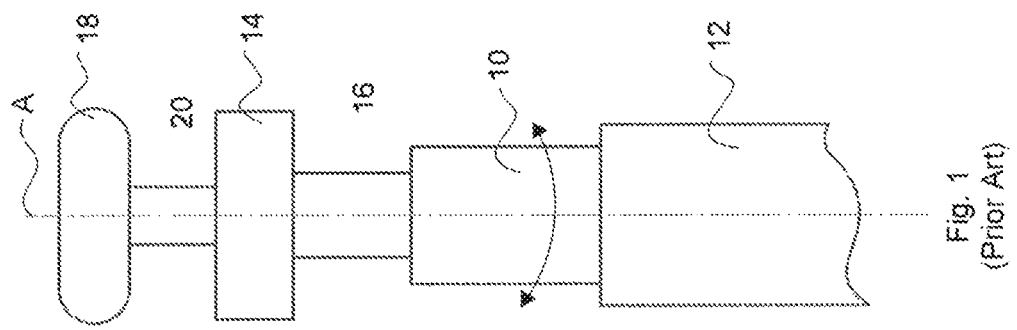
FIG. 1 is a schematic representation of a typical prior-art arrangement for measuring the torque applied to a rotating part.
Figure 2:
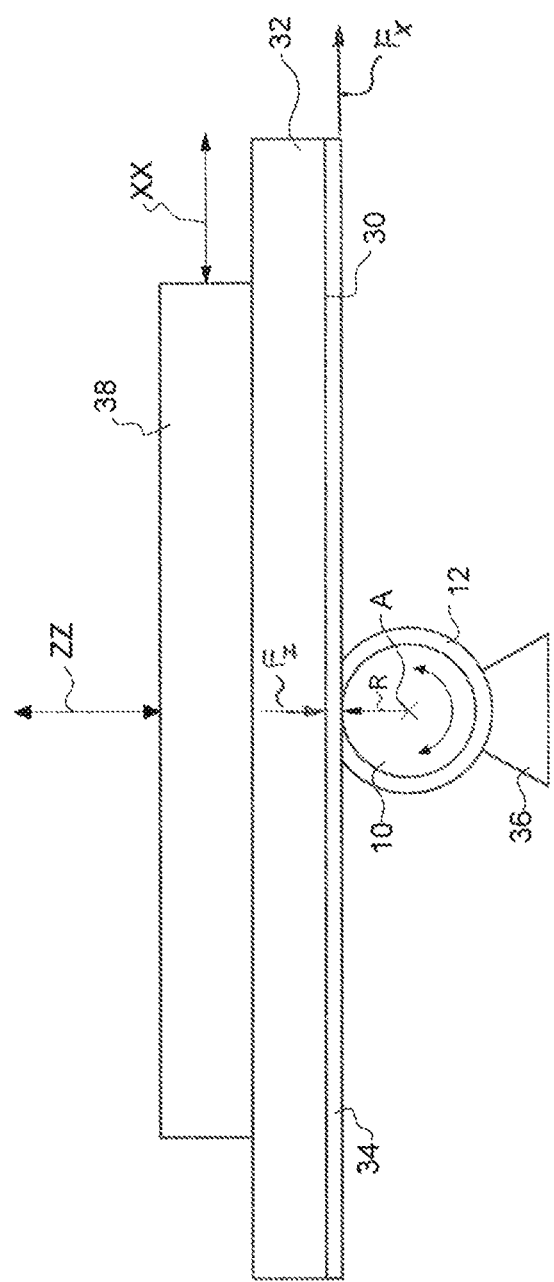
FIG. 2 is a schematic representation of the arrangement for measuring the torque applied to a rotating part using a two-dimensional force sensor according to the invention.

As illustrated schematically in FIG. 2, the invention is preferably carried out by connecting the planar side 30 of a 2-D force sensor 32, either directly or through a flat intermediate contact medium 34, tangentially to a test part or object 10 mounted on a bearing 12 supported by a normally stationary stage or structure 36. The force sensor 32 is coupled to a support mechanism 38 adapted for independent vertical and horizontal linear motions, such that the sensor 32 (or the intermediate medium 34) can be brought into contact with the cylindrical surface of the part 10 and moved horizontally along a direction normal to the axis of rotation A of the part. For the purposes of this description, the force sensor 32, the intermediate medium 34 for contacting the test part (if present), and the support mechanism 38 will hereinafter be referred to as the sensor assembly that is placed in tangential contact with the cylindrical surface of the part to be tested. It is understood that appropriate mechanisms are also required to translate the sensor assembly vertically and horizontally in both linear directions, as illustrated by arrows ZZ and XX in the figure. Alternatively, on in addition, the structure 36 may also be capable of translation in the ZZ and XX directions to produce the required relative motion of the sensor assembly with respect to the part under test.

Figure 3:
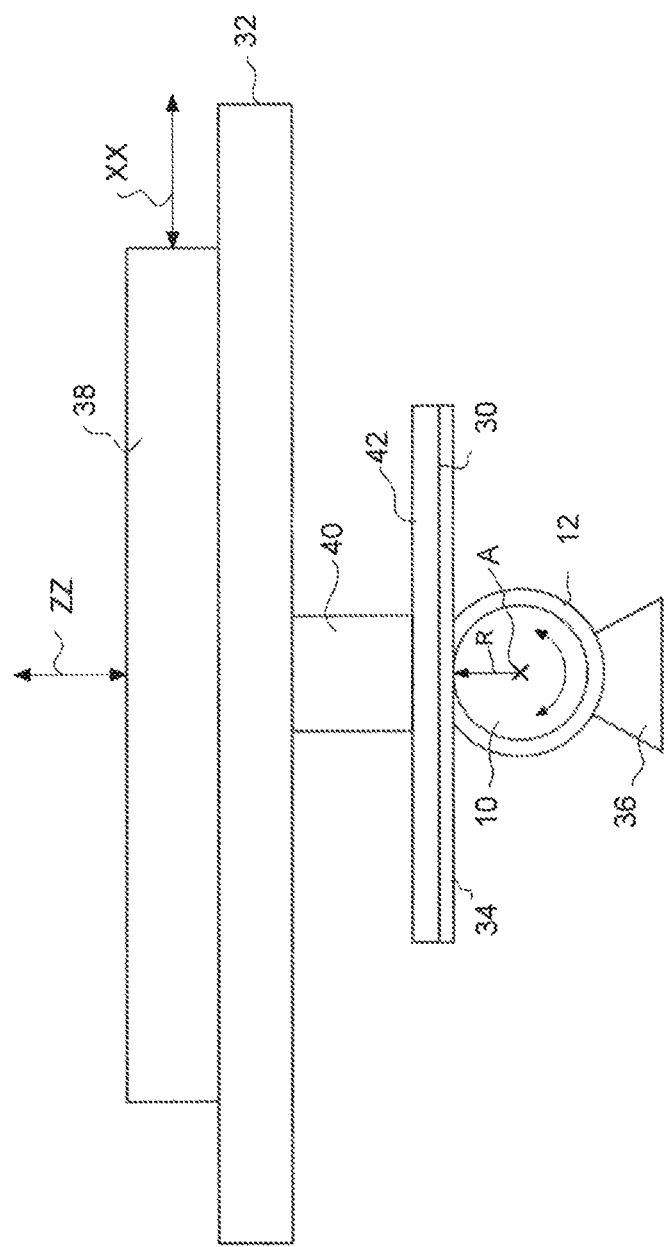
FIG. 3 is a schematic representation of an alternative embodiment of the invention of the invention.

In an alternative, currently preferred, embodiment of the invention illustrated in FIG. 3, an additional support structure 40 is used to couple the force sensor 32 to the medium 34 contacting the test part. The structure 40 may be a rigid rod, or similar structure, coupled to a distal planar component 42 to which the medium 34 may be attached. For the purposes of this description, if present, the structure 40 and the planar component 42 are also intended to be included in the definition of sensor assembly.

According to one aspect of the invention, the sensor assembly is brought into contact with the cylindrical surface of the part 10 (through either the flat surface 30 of the sensor or the medium 34) with a radial force $F_z$ that is just sufficient to ensure the non-slip frictional engagement of the part. Once the part 10 has been so contacted by the sensor assembly, a tangential force $F_x$ is applied to the part 10 by translating the sensor assembly laterally in a direction normal to the direction of application of $F_z$. The force $F_x$ is measured by the sensor and increased until the part 10 begins rotating around its axis A. The force is then decreased to the minimum required to maintain the constant-speed rotation of the part. Thus, the torque required to initiate and maintain the part's rotation is obtained simply by multiplying the values of the force $F_x$ recorded during the test by the radius R of the part.

The radial force $F_z$ that is applied to the part is readily measured by the sensor 32 and can be ascertained empirically by repeated trials with the same part. Thus, for inline measurement of copies of the same part for quality-control purposes during manufacture, the sensor assembly can be calibrated and programmed to always apply the correct amount of force $F_z$. By applying no more than the force required to ensure non-slip frictional contact, any potential deformation or damage to the part is minimized. Alternatively, especially when the same part is measured sequentially on a production line, the radial force $F_z$ can be constant and applied automatically without measurement, such as through a spring mechanism. In such cases, a linear force sensor aligned with the tangential direction of translation of the sensor assembly, can be used instead of a 2-D sensor.

Figure 4:
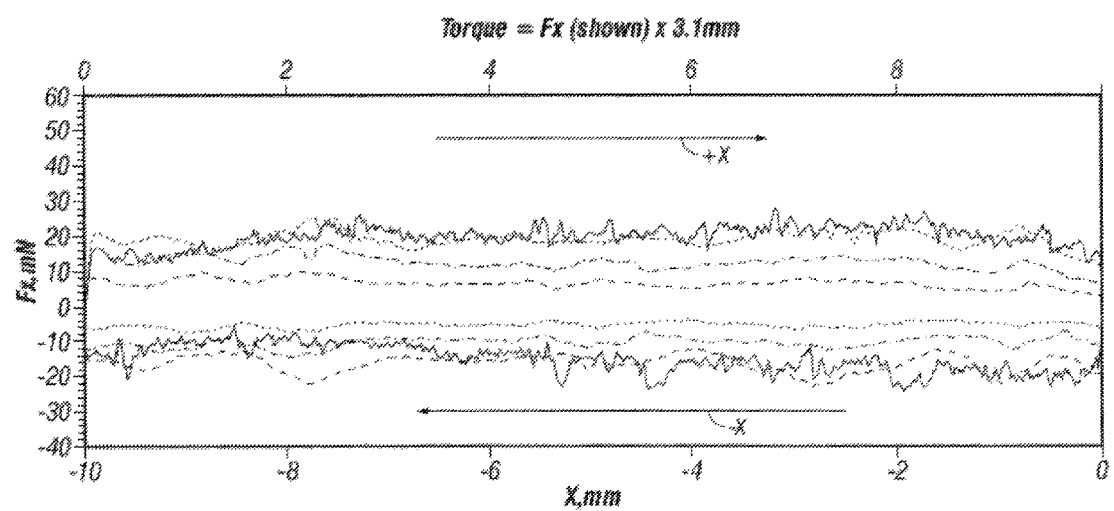
FIG. 4 is a collection of graphs illustrating the torque measured as a result of the progressively increasing application of a tangential force to an initially stationary rotating part.

FIG. 4 shows four sets of curves illustrating the torque measured by applying a force $F_x$ to an initially stationary cylindrical part with a 3.1-mm radius R supported by a very low friction bearing. The upper curves show the torque when the sensor assembly was translated in a positive X direction, while the lower curves correspond to sensor-assembly motion, and corresponding part rotation, in the opposite, negative X direction. The graph's abscissa shows the linear distance corresponding to the angular displacement produced by the rotation of the part during the test. As expected and experienced when torque is measured with strain gauges, each curve in the graph shows an initial rapid increase of the torque applied to overcome the inertia of the stationary part before rotation begins. Then, when the torque reaches the value required to maintain the part's rotation, it remains substantially constant during the duration of the test, as expected. Substantially the same results were obtained in both directions.

The torque values reported in FIG. 4 are all in the order of 20 Newton millimeters and less and, because of the relatively low noise associated with them, demonstrate the ability of the invention to measure torque at values not reliably measurable with prior-art approaches. In addition, because the part to be measured does not require axial alignment with the mechanism producing its rotation, the invention is ideal for inline, quality-control testing of parts during manufacture.

Two-dimensional force sensors are old and used for various applications. Such a sensor suitable for the invention is available, for example, from Bruker Nano Inc., Surfaces Division, of Campbell, Calif. As mentioned above, it is critical that the sensor assembly of the invention be coupled to the test part through a non-slip contact point. This can be accomplished by selecting appropriate materials for the surface of the sensor assembly contacting the part so as to ensure non-slip frictional engagement. Such contact may be direct between the part and the surface 30 of the sensor 32, or through the flat intermediate medium 34, such as made of rubber, attached to the sensor 32. The introduction of a material like rubber is preferred when the part to be tested could be damaged by contact with a metal surface.

Thus, a novel procedure has been described for testing very low values of a torque applied to a cylindrical object (or a cylindrical portion of an object) adapted for rotation around a predetermined axis. In summary, the flat surface of a 2-D force sensor is coupled, directly or through an intermediate medium, to the outer circumferential surface of the object to be tested. The sensor is oriented in such a way that it can exert and measure a force applied radially on the object and can also measure a force applied to the point of contact tangentially in a direction normal to the axis of rotation. The sensor is then translated linearly with respect to the object (or vice versa) in order to exert on the object a tangential frictional force that causes the object to rotate about its axis. The torque characteristics of the object are then calculated from the measured values of tangential force applied to the object and plotted as a function of the linear travel of the surface contacting the object. FIG. 5 illustrates the process in a flow chart. Alternatively, a one-dimensional force sensor can be used to measure the tangential force applied to the part. In such case a mechanism is used to provide the radial force required for frictional engagement of the sensor assembly with the part.

The invention has been described in terms of a sensor assembly that is translated tangentially in contact with a test object rotating over a stationary axis. However, it is understood that the invention could be practiced in equivalent fashion by translating the stage supporting the test object with respect to a stationary sensor assembly. The critical part of the invention is a force measured by a force sensor and applied tangentially to the cylindrical surface of the test object. Also, the invention has been described in terms of a vertical radial force $F_z$ and a horizontal tangential force $F_x$; however, it is understood that the two forces could be applied in any manner so long as radially and tangentially, respectively, and normal to each other.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in the drawing describing such embodiment, the presence of this detail in the drawing may be implied unless the context of the description requires otherwise. Furthermore, the described single features, structures, or characteristics of the invention may be combined in any suitable manner in one or more further embodiments.

While the invention has been shown and described herein with reference to what are believed to be the most practical embodiments, it is recognized that departures can be made within the scope of the invention and, therefore, the invention is not to be limited to the details disclosed herein but is to be accorded the full scope of equivalent articles.

We claim:

1. A method of measuring a torque applied to a rotatable object, the method comprising the following steps:
   providing a sensor assembly with a flat surface adapted for translation in orthogonal directions, said assembly including a force sensor;
   contacting a cylindrical surface of the object with said flat surface through the application of a radial force sufficient for frictional engagement of the object;
   applying a progressively increasing tangential force to said cylindrical surface of the object by translating the sensor assembly in a direction normal to an axis of rotation of the object, thereby causing the rotation of the object;
   measuring said tangential force with the force sensor during said step of applying the tangential force; and
   utilizing tangential-force values produced by the measuring step to determine torque characteristics of the rotatable object.

2. The method of claim 1, wherein said flat surface of the sensor assembly is a surface of the sensor.

3. The method of claim 1, wherein said flat surface of the sensor assembly is a rubber surface.

4. The method of claim 1, wherein said contacting step is carried out with a mechanism adapted to exert a predetermined radial force on said cylindrical surface of the object.

5. The method of claim 4, wherein the mechanism includes a spring-loaded component.

6. The method of claim 4, wherein said flat surface of the sensor assembly is a surface of the sensor.

7. The method of claim 4, wherein said flat surface of the sensor assembly is a rubber surface.

8. The method of claim 1, wherein said force sensor is a two-dimensional force sensor, and said contacting step is carried out by measuring said radial force applied on the cylindrical surface of the object.

9. The method of claim 8, wherein said flat surface of the sensor assembly is a surface of the sensor.

10. The method of claim 8, wherein said flat surface of the sensor assembly is a rubber surface.

11. A method of measuring a torque applied to a rotatable object mounted on a support structure, the method comprising the following steps:
    providing a sensor assembly with a flat surface adapted for engaging the rotatable object, said assembly including a force sensor;
    contacting a cylindrical surface of the object with said flat surface through the application of a radial force sufficient for frictional engagement of the object;
    applying a progressively increasing tangential force to said cylindrical surface of the object in a direction normal to an axis of rotation of the object, thereby causing the rotation of the object;
    measuring said tangential force with the force sensor during said step of applying the tangential force; and
    utilizing tangential-force values produced by the measuring step to determine torque characteristics of the rotatable object.

12. The method of claim 11, wherein said flat surface of the sensor assembly is a surface of the sensor.

13. The method of claim 11, wherein said flat surface of the sensor assembly is a rubber surface.

14. The method of claim 11, wherein said contacting step is carried out with a mechanism adapted to exert a predetermined radial force on said cylindrical surface of the object.

15. The method of claim 14, wherein the mechanism includes a spring-loaded component.

16. The method of claim 11, wherein said step of applying a tangential force is carried out by translating the sensor assembly in relation to said support structure of the object.

17. The method of claim 11, wherein said step of applying a tangential force is carried out by translating said support structure of the object in relation to the sensor assembly.

18. The method of claim 11, wherein said force sensor is a two-dimensional force sensor, and said contacting step is carried out by measuring said radial force applied on the cylindrical surface of the object.

19. The method of claim 18, wherein said flat surface of the sensor assembly is a surface of the sensor.

20. The method of claim 18, wherein said flat surface of the sensor assembly is a rubber surface.

* * * * *